United States Patent
Yoshimura et al.

(10) Patent No.: US 9,528,998 B2
(45) Date of Patent: Dec. 27, 2016

(54) METHODS AND REAGENTS FOR DIAGNOSING RHEUMATOID ARTHRTIS

(75) Inventors: Toru Yoshimura, Matsudo (JP); Ryotaro Chiba, Matsudo (JP)

(73) Assignee: ABBOTT LABORATORIES, Abbott Park, IL (US)

( * ) Notice: Subject to any disclaimer, the term of this patent is extended or adjusted under 35 U.S.C. 154(b) by 233 days.

(21) Appl. No.: 13/086,528

(22) Filed: Apr. 14, 2011

(65) Prior Publication Data

US 2011/0256636 A1    Oct. 20, 2011

Related U.S. Application Data

(60) Provisional application No. 61/325,027, filed on Apr. 16, 2010.

(51) Int. Cl.
G01N 33/68    (2006.01)

(52) U.S. Cl.
CPC ...... G01N 33/6863 (2013.01); G01N 33/6803 (2013.01); G01N 33/6854 (2013.01); G01N 2800/102 (2013.01)

(58) Field of Classification Search
CPC ......... C07K 16/18; C07K 16/24; C07K 16/40; C07K 16/42; G01N 33/68; G01N 33/6854; G01N 33/6863; G01N 33/573; G01N 2333/4724; G01N 2333/4737; G01N 2333/523; G01N 2333/96494; G01N 2800/102; G01N 33/6803

USPC ....... 435/7.1, 7.21, 7.24, 7.4, 7.92, 7.94, 23, 435/973, 975; 546/501, 506, 509, 518, 425/523, 546/164, 172, 811; 530/388.23, 530/388.24, 388.25, 388.26, 388.7, 389.2, 530/389.3, 389.6, 391.1, 391.3
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |

(Continued)

FOREIGN PATENT DOCUMENTS

| | | |
|---|---|---|
| EP | 0471293 A2 | 2/1992 |
| EP | 2163896 A1 | 3/2010 |

(Continued)

OTHER PUBLICATIONS

Pierer et al., 2004. Chemokine secretion of rheumatoid arthritis synovial fibroblasts stimulated by Toll-like receptor 2 ligands. J. Immunol. 172: 1256-1265.*

(Continued)

*Primary Examiner* — Gail R Gabel
(74) *Attorney, Agent, or Firm* — Irene M. Reininger

(57) ABSTRACT

Methods for diagnosing rheumatoid arthritis (RA) are disclosed, using measurement of the CCL8 protein level in a test sample from a subject. Testing for CCL8 as an indicator of RA can be combined with testing for other indicators of RA, including clinical assessments, imaging or other RA markers such as Rheumatoid factor (RF). CCL8 testing can be used for discriminating RA from other diseases or conditions, evaluating the severity of RA. Related diagnostic reagents, kits, pharmaceutical compositions, and methods for identifying a candidate substance as a therapeutic agent for treating rheumatoid arthritis are also described.

3 Claims, 2 Drawing Sheets

(56) References Cited

U.S. PATENT DOCUMENTS

| | | | |
|---|---|---|---|
| 5,006,309 | A | 4/1991 | Khalil et al. |
| 5,063,081 | A | 11/1991 | Cozzette et al. |
| 5,089,424 | A | 2/1992 | Khalil et al. |
| 5,135,875 | A | 8/1992 | Meucci et al. |
| 5,241,070 | A | 8/1993 | Law |
| 5,294,404 | A | 3/1994 | Grandone et al. |
| 5,352,803 | A | 10/1994 | Mattingly |
| 5,359,093 | A | 10/1994 | Adamczyk et al. |
| 5,468,646 | A | 11/1995 | Mattingly et al. |
| 5,480,792 | A | 1/1996 | Buechler et al. |
| 5,496,925 | A | 3/1996 | Mattingly |
| 5,525,524 | A | 6/1996 | Buechler et al. |
| 5,543,524 | A | 8/1996 | Mattingly et al. |
| 5,573,904 | A | 11/1996 | Mattingly |
| 5,593,896 | A | 1/1997 | Adamczyk et al. |
| 5,783,699 | A | 7/1998 | Mattingly et al. |
| 5,824,799 | A | 10/1998 | Buechler et al. |
| 5,834,212 | A * | 11/1998 | Okada et al. ............... 435/7.4 |
| 5,851,776 | A | 12/1998 | Valkirs |
| 5,885,527 | A | 3/1999 | Buechler |
| 5,922,615 | A | 7/1999 | Nowakowski et al. |
| 5,939,272 | A | 8/1999 | Buechler et al. |
| 5,947,124 | A | 9/1999 | Buechler et al. |
| 5,985,579 | A | 11/1999 | Buechler et al. |
| 6,019,944 | A | 2/2000 | Buechler |
| 6,113,855 | A | 9/2000 | Buechler |
| 6,143,576 | A | 11/2000 | Buechler |
| 6,890,763 | B2 | 5/2005 | Jackowski et al. |
| 6,925,389 | B2 | 8/2005 | Hitt et al. |
| 6,989,100 | B2 | 1/2006 | Norton |
| 7,060,504 | B2 | 6/2006 | Tracey et al. |
| 7,906,293 | B2 | 3/2011 | Mattingly et al. |
| 7,964,194 | B2 * | 6/2011 | Lillard et al. ............. 424/145.1 |
| 8,445,199 | B2 | 5/2013 | Collier et al. |
| 2003/0170881 | A1 | 9/2003 | Davis et al. |
| 2003/0224386 | A1 * | 12/2003 | Guild et al. ..................... 435/6 |
| 2004/0009503 | A1 * | 1/2004 | Fu et al. ........................ 435/6 |
| 2004/0018577 | A1 | 1/2004 | Emerson Campbell et al. |
| 2004/0248158 | A1 * | 12/2004 | Loughran et al. ................ 435/6 |
| 2005/0025768 | A1 * | 2/2005 | De Fougerolles et al. ............. 424/145.1 |
| 2005/0054078 | A1 | 3/2005 | Miller et al. |
| 2006/0134706 | A1 | 6/2006 | Hide et al. |
| 2006/0160164 | A1 | 7/2006 | Miller et al. |
| 2007/0072237 | A1 * | 3/2007 | Wild et al. .................... 435/7.1 |
| 2007/0099239 | A1 | 5/2007 | Tabibiazar et al. |
| 2008/0020401 | A1 | 1/2008 | Grenier et al. |
| 2011/0256636 | A1 | 10/2011 | Yoshimura et al. |

FOREIGN PATENT DOCUMENTS

| | | |
|---|---|---|
| WO | 2005005474 A1 | 1/2005 |
| WO | 2008037420 A1 | 4/2008 |
| WO | 2008128987 A1 | 10/2008 |
| WO | WO2009001545 A1 | 12/2008 |

OTHER PUBLICATIONS

Distler et al., 2005. The induction of matrix metalloproteinase and cytokine expression in synovial fibroblasts stimulated with immune cell microparticles. PNAS 102: 2892-2897 and Supplementary information.*

Galligan et al., 2007. Distinctive gene expression signatures in rheumatoid arthritis synovial tissue fibroblast cells: correlates with disease activity. Genes and Immunity 8: 480-491.*

Keyszer et al., 1999. Circulating levels of matrix metalloproteinases MMP-3 and MMP-1, tissue inhibitor of metalloproteinases 1 (TIMP-1), and MMP-1/TIMP-1 complex in rheumatic disease. J. Rheumatol. 26: 251-258.*

Marcelletti et al., 2003. Assessment of serological markers associated with rheumatoid arthritis. Diagnostic autoantibodies and conventional disease activity markers. Clin. Appl. Immunol. Rev. 4: 109-123.*

Kudo-Tanaka et al., 2007. Autoantibodies to cyclic citrullinated peptide 2 (CCP2) are superior to other potential diagnostic biomarkers for predicting rheumatoid arthritis in early undifferentiated arthritis. Clin Rheumatol. 26: 1627-1633.*

Lu et al., 2007. Comparison of anti-agalactosyl IgG antibodies, rheumatoid factors, and anti-cyclic citrullinated peptide antibodies in the differential diagnosis of rheumatoid arthritis and its mimics. Clin. Exp. Rheumatol. 25 : 716-721.*

Sakai et al., 2009. Efficacy of high-throughput leukocytapheresis for rheumatoid arthritis with a reduced response to Infliximab. Therapeutic Apheresis and Dialysis 13: 179-185.*

Arnett et al., 1988. The American Rheumatism Association 1987 revised criteria for the classification of rheumatoid arthritis. Arth. Rheumatism 31: 315-324.*

Arnett F.C., et al., "The American Rheumatism Association 1987 Revised Criteria for the Classification of Rheumatoid Arthritis," Arthritis and Rheumatism, 1988, vol. 31 (3), pp. 315-324.

Asai D.J., "Antibodies in Cell Biology," in: Methods in Cell Biology, Academic Press Inc., 1993, vol. 37, Table of Contents.

Clackson T., et al., "Making Antibody Fragments Using Phage Display Libraries," Nature, 1991, vol. 352 (6336), pp. 624-628.

Coligan J.E., et al., eds., "Peptides," in: Current Protocols in Immunology, John Wiley & Sons, vol. 2, 1991. pp. 9.0.1-9.4.11.

Griffiths A.D., et al., "Human Anti-Self Antibodies with High Specificity From Phage Display Libraries," The EMBO Journal, 1993, vol. 12 (2), pp. 725-734.

Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.

Hori T., et al., "CCL8 is a Potential Molecular Candidate for the Diagnosis of Graft-Versus-Host Disease," Blood, 2008, vol. 111 (8), pp. 4403-4412.

Kohler G., et al., "Continuous Cultures of Fused Cells Secreting Antibody of Predefined Specificity," Nature, 1975, vol. 256 (5517), pp. 495-497.

Marks J.D., et al., "By-passing Immunization. Human Antibodies from V-gene Libraries Displayed on Phage," Journal of Molecular Biology, 1991, vol. 222, pp. 581-597.

Marks J.D., et al., "By-Passing Immunization: Building High Affinity Human Antibodies by Chain Shuffling," Bio Technology, 1992, vol. 10 (7), pp. 779-783.

McCafferty J., et al., "Phage Antibodies: Filamentous Phage Displaying Antibody Variable Domains," Nature, 1990, vol. 348, pp. 552-554.

Robinson J.R., Sustained and Controlled Release Drug Delivery Systems, Marcel Dekker, Inc., 1978, Table of Contents.

Stites D.P., et al., eds., "Basic and Clinical Immunology," 7th Edition, Appleton & Lange, 1991, Table of Contents.

Vaitukaitis J.L., "Production of Antisera with Small Doses of Immunogen: Multiple Intradermal Injections," Methods in Enzymology, 1981, vol. 73 (Pt B), pp. 46-52.

Haringman J.J., et al., "Chemokine and Chemokine Receptor Expression in Paired Peripheral Blood Mononuclear Cells and Synovial Tissue of Patients with Rheumatoid Arthritis, Osteoarthritis, and Reactive Arthritis," Annals of the Rheumatic Diseases, 2006, vol. 65 (3), pp. 294-300.

Written Opinion for Application No. PCT/JP2011/059226, mailed on Jun. 28, 2011, 4 pages.

Adamczyk M., et al., "Chemiluminescence Quenching of Pteroic Acid-N-sulfonyl-acridinium-9-carboxamide Conjugates by Folate Binding Protein," Bioorganic and Medicinal Chemistry Letters, 2004, vol. 14 (9), pp. 2313-2317.

Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters, 2006, vol. 16 (5), pp. 1324-1328.

Adamczyk M., et al., "Chemiluminescent N-Sulfonylacridinium-9-Carboxamides and Their Application in Clinical Assays ," Luminescence Biotechnology: Instruments and Applications , 2002, pp. 77-105.

(56) References Cited

OTHER PUBLICATIONS

Adamczyk M., et al., "Homogeneous Chemiluminescent Assays for Free Choline in Human Plasma and Whole Blood ," Analytica Chimica Acta, 2006, vol. 579 (1), pp. 61-67.

Adamczyk M., et al., "Intrinsic Factor-Mediated Modulation of Cyanocobalamin-N-sulfonyl-acridinium-9-carboxamide Chemiluminescence," Bioorganic and Medicinal Chemistry Letters, 2004, vol. 14 (15), pp. 3917-3921.

Adamczyk M., et al., "Linker-Mediated Modulation of the Chemiluminescent Signal from N10-(3-Sulfopropyl)-N-Sulfonylacridinium-9-carboxamide Tracers," Bioconjugate Chemistry, 2000, vol. 11 (5), pp. 714-724.

Adamczyk M., et al., "Modulation of the Chemiluminescent Signal from N10-(3-Sulfopropyl)-N-Sulfonylacridinium-9-carboxamides," Tetrahedron, 1999, vol. 55, pp. 10899-10914.

Adamczyk M., et al., "Neopentyl 3-Triflyloxypropanesulfonate a Reactive Sulfopropylation Reagent for the Preparation of Chemiluminescent Labels," Journal of Organic Chemistry, 1998, vol. 63, pp. 5636-5639.

Adamczyk M., et al., "Regiodependent Luminescence Quenching of Biotinylated N-Sulfonyl-acridinium-9-carboxamides by Avidin ," Organic Letters, 2003, vol. 5 (21), pp. 3779-3782.

Adamczyk M., et al., "Synthesis of a Chemiluminescent Acridinium Hydroxylamine (AHA) for the Direct Detection of Abasic Sites in DNA," Organic Letters , 1999, vol. 1 (5), pp. 779-781.

Aletaha D., et al., "2010 Rheumatoid Arthritis Classification Criteria: An American College of Rheumatology/European League Against Rheumatism Collaborative Initiative," Annals of the Rheumatic Diseases, 2010, vol. 69 (9), pp. 1580-1588.

Chong B.F., et al., "E-Selectin, Thymus- and Activation-regulated Chemokine/CCL17, and Intercellular Adhesion Molecule-1 are Constitutively Coexpressed in Dermal Microvessels: A Foundation for a Cutaneous Immunosurveillance System," Journal of Immunology, 2004, vol. 172 (3), pp. 1575-1581.

Co-pending U.S. Appl. No. 61/142,048, filed Dec. 31, 2008.

Furusyo N., et al., "Thymus and Activation Regulated Chemokines in Children with Atopic Dermatitis: Kyushu University Ishigaki Atopic Dermatitis Study (KIDS)," European Journal of Dermatology, 2007, vol. 17 (5), pp. 397-404.

Heagerty P.J., et al., "Time-Dependent ROC Curves for Censored Survival Data and a Diagnostic Marker," Biometrics, 2000, vol. 56 (2), pp. 337-344.

Imai T., et al., "The T Cell-directed CC Chemokine TARC is a Highly Specific Biological Ligand for CC Chemokine Receptor 4," Journal of Biological Chemistry, 1997, vol. 273 (23), pp. 15036-15042.

International Search Report for Application No. PCT/JP2011/059226, mailed on Jun. 28, 2011, 3 pages.

Kakinuma T., et al., "Thymus and Activation-regulated Chemokine in Atopic Dermatitis: Serum Thymus and Activation-regulated Chemokine Level is Closely Related with Disease Activity," Journal of Allergy and Clinical Immunology, 2001, vol. 107 (3), pp. 535-541.

Mattingly P.G., "Chemiluminescent 10-Methyl-Acridinium-9(N-Sulphonylcarboxamide) Salts. Synthesis and Kinetics of Light Emission," Journal of Bioluminescence and Chemiluminescence, 1991, vol. 6 (2), pp. 107-114.

McCapra F., et al., "Chemiluminescence Involving Peroxide Decompositions ," Photochemistry and Photobiology, 1965, vol. 4, pp. 1111-1121.

Morita A., et al., "Evaluation of Human Thymus and Activation-regulated Chemokine Concentrations in Blood Using a New Sandwich ELISA Based on Monoclonal Antibodies," Clinica Chimica Acta, 2002, vol. 322 (1-2), pp. 67-75.

Razavi Z., et al., "Stable and Versatile Active Acridinium Esters I ," Luminescence, 2000, vol. 15 (4), pp. 239-244.

Razavi Z., et al., "Stable and Versatile Active Acridinium Esters II," Luminescence, 2000, vol. 15, pp. 245-249.

Takeuchi H., et al., "Changes in Thymus- and Activation-regulated Chemokine (TARC) Associated with Allergen Immunotherapy in Patients with Perennial Allergic Rhinitis," Journal of Investigational Allergology and Clinical Immunology, 2005, vol. 15 (3), pp. 172-176.

Wallemacq P.E., et al., "Evaluation of the New AxSYM Cyclosporine Assay: Comparison with TDx Monoclonal Whole Blood and Emit Cyclosporine Assays," Clinical Chemistry, 1999, vol. 45 (3), pp. 432-435.

Quantikine, Human TARC Immunoassay, Catalog No. DDN00, SDN00, PDDN00, R&D Systems, Inc, 2010, 15 pages.

Aggarwal, A. et al., "Chemokine and chemokine receptor analysis reveals elevated interferon-inducible protein-10 (IP)-10/CXCL10 levels and increased number of CCR5+ and CXCR3+ CD4 T cells in synovial fluid of patients with enthesitis-related arthritis (ERA)," Clin. Exp. Immunol. (2007) 148:515-519.

Avouac, J. et al., "Diagnostic and predictive value of anti-cyclic citrullinated protein antibodies in rheumatoid arthritis: a systematic literature review," Ann. Rheum. Dis. (2006) 65:845-851.

Ho, C.Y. et al., "Suppressive effect of combination treatment of leflunomide and methotrexate on chemokine expression in pateitns with rheumatoid arthritis," Clin. Exp. Immunol. (2003) 133:132-138.

Radstake, T.R.D.J. etal., "Increased expression of CCL18, CCL19, and CCL17 by dendritic cells from patients with rheumatoid arthritis, and regulation by Fc gamma receptors," Ann. Rheum. Dis. (2005) 64:359-367.

TARC, Thymus and Activation-Regulated Chemokine, CCL17 ELISA Shionogi, 2008, 16 pages.

United States Patent Office Action for U.S. Appl. No. 13/728,003 dated Apr. 16, 2015 (9 pages).

United States Patent Office Action for U.S. Appl. No. 13/728,003 dated Dec. 26, 2014 (9 pages).

\* cited by examiner

METHODS AND REAGENTS FOR DIAGNOSING RHEUMATOID ARTHRTIS

REFERENCE TO RELATED APPLICATIONS

This application claims priority to U.S. Provisional Application Ser. No. 61/325,027 filed Apr. 16, 2010, which is incorporated by reference in its entirety.

FIELD OF THE INVENTION

The present disclosure relates to biomarkers of disease and more particularly to a novel biomarker of rheumatoid arthritis, to related methods involving use of the marker including diagnostic methods, and also to reagents and therapeutic compositions including the biomarker.

BACKGROUND

Rheumatoid arthritis (RA) is a serious, chronic autoimmune disease that afflicts about 1% of the world's population. Women are affected three times more often than men. RA primarily attacks the joints, where an inflammatory synovitis frequently destroys articular cartilage and causes ankylosis. RA may involve other tissues in diffuse inflammation including lungs, pericardium, pleura, and sclera. RA is both crippling and painful, and frequently leads to substantial loss of mobility and overall function.

Diagnosis of RA is typically based initially on clinical signs and symptoms, but because the clinical indicators of RA are shared with a number of other common diseases and conditions, the clinical evaluation is usually supplemented by X-rays, and by blood tests for known markers, such as rheumatoid factor (RF). Thus, when RA is suspected from observation of clinical signs and symptoms, blood tests such as those testing for the presence of RF are typically used to help confirm a diagnosis. Known markers however do not necessarily detect RA with a very high level of sensitivity to RA and specificity for RA. For example, particularly during the earliest stages of RA in the first year, about 15-20% of patients do not seroconvert to RF and therefore an RF test on such a patient during this time will produce a false negative result. Moreover, RF is not 100% specific to RA, being present in about 10% of the healthy population and also in individuals with other inflammatory diseases or conditions, especially Sjögren's syndrome but also chronic hepatitis, any chronic viral infection, leukemia, dermatomyositis, infectious mononucleosis, systemic sclerosis and systemic lupus erythematosus. RF tests on such individuals will produce a significant number of false positive results. Serological markers of RA also include anti-citrullinated protein antibodies (ACPAs), as tested in the anti-CCP (cyclic citrullinated peptide) test and the anti-MCV (antibodies against mutated citrullinated Vimentin) assay, which also produce significant numbers of false positive and/or false positive results with respect to RA. Markers of RA with improved sensitivity to and specificity for RA are needed so that positive diagnoses of RA can be confirmed as early as possible in the course of the disease.

SUMMARY OF THE INVENTION

The present disclosure shows that the level of CCL-8 (Chemokine c-c motif Ligand 8) protein in a blood sample from a subject is a positive indicator of the presence of rheumatoid arthritis in the subject, with a high level of sensitivity and specificity. Moreover, levels of CCL8 in the blood are positively correlated with the severity of the disease in the subject, such that, for example, an elevated level of CCL8 in the blood indicates a severe case of rheumatoid arthritis.

Accordingly, in one aspect, the present disclosure provides a method for diagnosing rheumatoid arthritis in a subject comprising measuring the level of CCL8 protein in a test sample obtained from the subject wherein the level of CCL8 protein in the test sample indicates presence or absence of rheumatoid arthritis in the subject. The presence or absence of rheumatoid arthritis can be determined before clinical indicators of rheumatoid arthritis are present in the subject. The level of CCL8 protein in the test sample can be measured for example using an anti-CCL8 antibody. The test sample can be a blood sample including a plasma or a serum sample. The method may further comprise measuring the level of one or more additional markers of rheumatoid arthritis in the sample, wherein the level of each additional marker in the test sample further indicates presence or absence of rheumatoid arthritis in the subject. Such markers include for example CRP, a-CCP, CARF IgG, MMP-3 and Rheumatoid factor.

In another aspect the present disclosure provides a method for determining the severity of rheumatoid arthritis in a subject comprising determining the presence or absence of an elevated level of CCL8 protein in a test sample obtained from the subject wherein the presence of an elevated level of CCL8 protein indicates that the rheumatoid arthritis in the subject is severe. The method may further comprise measuring the level of one or more markers of rheumatoid arthritis in the sample wherein the markers are selected from the group consisting of: CRP, a-CCP, CARF IgG, MMP-3 and Rheumatoid factor, wherein the level of the one or markers in the test sample further indicates presence or absence of rheumatoid arthritis in the subject.

In another aspect the present disclosure provides a diagnostic reagent for rheumatoid arthritis comprising an anti-CCL8 antibody or fragment thereof, and an antibody against at least one marker of rheumatoid arthritis selected from the group consisting of: CRP, a-CCP, CARF IgG, MMP-3 and Rheumatoid factor. The diagnostic reagent may be included in a diagnostic kit.

In another aspect the present disclosure provides a method for identifying a candidate substance as a therapeutic agent for treating rheumatoid arthritis, comprising: a) administering a test substance to an animal subject having an animal model of rheumatoid arthritis; b) measuring the level of CCL8 protein in a test sample obtained from the animal subject; and c) selecting the test substance as a candidate substance as a therapeutic agent for treating rheumatoid arthritis substance if the level of CCL8 protein in the test sample is lower than the level of CCL8 protein in a test sample from a comparable animal subject not administered the test substance.

In another aspect the present disclosure encompasses use of an anti-CCL8 antibody or fragment thereof as a diagnostic reagent for the diagnosis of rheumatoid arthritis in a subject.

In another aspect the present disclosure encompasses use of an anti-CCL8 antibody or fragment thereof as an active ingredient in a pharmaceutical composition for the treatment of rheumatoid arthritis in a subject.

In another aspect the present disclosure encompasses use of an anti-CCL8 antibody or fragment thereof in the manufacture of a reagent for the diagnosis of rheumatoid arthritis in a subject.

In another aspect the present disclosure encompasses use of an anti-CCL8 antibody or fragment thereof in the manufacture of a pharmaceutical composition for the treatment of rheumatoid arthritis in a subject.

In another aspect the present disclosure provides a method for monitoring the effect of a treatment of rheumatoid arthritis in a subject comprising: a) measuring a first level of CCL8 protein in a first test sample obtained from the subject before the treatment; b) measuring a second level of CCL8 protein in a second test sample obtained from the subject after the treatment begins; and c) comparing the first level of CCL8 protein and the second level of CCL8 protein, wherein a second level of CCL8 protein level that is lower than the first level of CCL8 protein is indicative of a therapeutic effect of the treatment in the subject.

In any of the above methods, the level of CCL8 protein in the test sample can be measured for example using an anti-CCL8 antibody. In any of the above methods, the test sample(s) can be blood samples including plasma or serum samples. In any of the above methods, the level of CCL8 protein can be measured using a method selected from the group consisting of: mass spectrometry, high performance liquid chromatography, and two-dimensional electrophoresis.

DETAILED DESCRIPTION OF THE INVENTION

Figure 1:
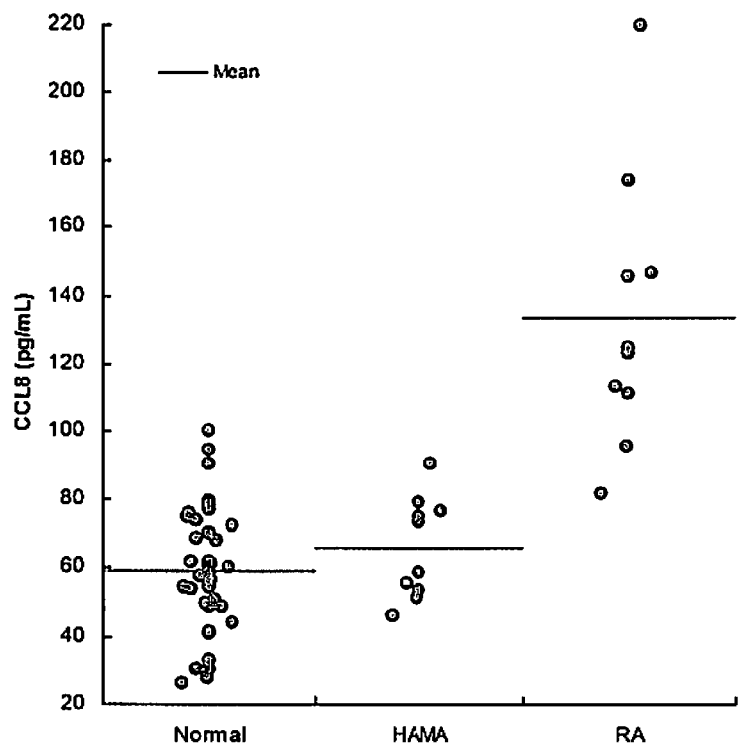
FIG. 1 is a scatter plot of CCL8 levels measured in blood serum samples from normal individuals, individuals exhibiting Human anti-mouse antibody response (HAMA), and individuals with a positive diagnosis of rheumatoid arthritis (RA).

The present disclosure describes the surprising finding that the level of CCL-8 (Chemokine c-c motif Ligand 8) in blood is a positive indicator of the presence of rheumatoid arthritis (RA) in a subject, with a low false positive rate. While CCL8 protein has been recognized as a marker of graft versus host disease following hematopoietic stem cell transplant (Blood 111, 4403-4412 (2008), WO2009001545 (A1)), that CCL8 bears any relationship to RA has not been disclosed or demonstrated until now. Thus, for example, the present disclosure provides that a blood level of CCL8 protein in a subject above a predetermined cut-off can be used as the basis for a diagnostic test for the presence of RA, even before the appearance of clinical signs of the disease in the subject. Moreover, the blood level of CCL8 protein in a subject positively correlates with the severity of RA disease in the subject, such that an elevated blood level of CCL8 indicates a severe case of RA in the subject. Methods that can be used to measure CCL8 level in a test sample include for example immunoassay methods, although other methods can be used. Related methods, reagents and compositions are also described.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Antibody

As used herein, the term "antibody" refers to a protein consisting of one or more polypeptides substantially encoded by immunoglobulin genes or fragments of immunoglobulin genes, and encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

b) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like. Preferred detectable labels include acridinium compounds such as an acridinium-9-carboximide having a structure according to Formula I as set forth in section B herein below, and an acridinium-9-carboxylate aryl ester having a structure according to Formula II as also set forth in section B herein below.

c) Marker

The terms "marker" or "biomarker" as used interchangeably herein refer to any molecule used as a target for analyzing test samples obtained from subjects, and encompass proteins or polypeptides themselves as well as antibodies against same that may be present in a test sample. Proteins or polypeptides used as a marker include any variants and fragments thereof, and in particular, immunologically detectable fragments. For example, it will be appreciated that variants of a marker polypeptide are encoded by the same gene, but can differ in their isoelectric point or molecular weight or both as a result of alternative processing such as alternative splicing and/or differences in post-translational modification (e.g., glycosylation, acylation, and/or phosphorylation). It will further be appreciated that cellular proteins can be damaged as a result of a disease process such as inflammation and may fragment and thus that proteins or polypeptides used as a marker according to the present disclosure include fragments thereof. Additionally it will be recognized that certain markers can be synthesized in an inactive form that is subsequently converted to an active form by proteolysis. Proteins or fragments thereof can also occur as part of a complex. Proteins or polypeptides used as markers according to the present disclosure also include such complexes.

d) Subject

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

e) Test Sample

As used herein, the term "test sample" generally refers to a biological material being tested for and/or suspected of containing an analyte of interest. The biological material may be derived from any biological source but preferably is a biological fluid likely to contain the analyte of interest. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. Preferably, the test sample is a serum or plasma sample.

The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that the analyte of interest remains in the test sample at a concentration proportional to that in an untreated test sample (e.g., namely, a test sample that is not subjected to any such pretreatment method(s)).

B. Methods

Methods according to the present disclosure include a method for diagnosing rheumatoid arthritis in a subject, according to which the level of CCL8 protein in a test sample obtained from the subject is measured. The test sample is for example whole blood, serum or plasma sample that is obtained from the patient using any commonly used phlebotomy method, such as a needle-stick, and discarded following testing. It will be appreciated that although the high level of specificity and sensitivity for RA demonstrated by CCL8 protein supports its stand-alone use for diagnosing RA, typically the diagnostic method will be used together with other indicators of RA, including at least a clinical assessment of the subject and possibly also X-ray and, or in the alternative, in vitro tests for the presence of other markers of RA, including CRP, a-CCP, CARF IgG, MMP-3 and Rheumatoid factor (RF). The methods described herein can be used to determine the presence or absence of RA before any clinical indicators of rheumatoid arthritis are noted as present in the subject. No biochemical marker however, is diagnostic for RA with 100% specificity and 100% sensitivity. It will therefore be appreciated that each biochemical marker can be used to determine with a certain level of probability that a RA is present or absent in a subject. Thus, the methods according to the present disclosure provide additional tools to aid in determining the presence or absence of RA. The methods can be especially useful for example in discriminating RA from other diseases or conditions with comparable clinical signs or symptoms, such as osteoarthritis.

Accepted clinical indicators of RA include those set forth by the American College of Rheumatology as Revised Criteria for the Classification of RA (Arnett, F. C., et al., Arthritis Rheum 31 (1988) 315-324; "ARA criteria"). The ARA-criteria provide that a patient has RA upon satisfying at least four of the following criteria, wherein criteria 1-4 must be present for at least six weeks: 1) morning stiffness for at least one hour, 2) arthritis of three or more joint areas, 3) arthritis of hand joints, 4) symmetrical arthritis, 5) rheumatoid nodules, 6) serum rheumatoid factor ("RF"), and 7) radiographic changes. The ARA criteria have demonstrated a sensitivity and specificity of approximately 90%. The diagnostic method according to the present disclosure will therefore assist the physician in establishing a firm diagnosis of RA, for example the presence or absence of RA in the patient.

The level of CCL8 protein can be measured according to any known specific binding method for determining the level of a protein or peptide analyte in a test sample, including any immunoassay technique as are well known in the art. Immunoassays involve the use of an antibody as a specific binding partner for the analyte of interest, including for example CCL8 protein, i.e. an anti-CCL8 antibody. An immunoassay for CCL8 protein as a marker of Graft-versus-host disease (GVHD) is described for example in T. Hori and Y. Kokai, BLOOD 111, 4403-4412 (2008), WO2009001545 (A1) and EP Application No. 20088764208 filed Jun. 23, 2008, the disclosures of which are hereby incorporated by reference in their entireties. Suitable immunoassay methods can be carried out in any of a wide variety of formats. A general review of immunoassays is available in METHODS IN CELL BIOLOGY VOLUME 37: ANTIBODIES IN CELL BIOLOGY, Asai, ed. Academic Press, Inc. New York (1993), and BASIC AND CLINICAL IMMUNOLOGY 7TH EDITION, Stites & Terr, eds. (1991), which are herein incorporated by reference in their entireties.

The methods involve correlating a CCL8 protein level to the presence or absence of RA, which can be performed in any of several different ways. For example, a reference population, typically a normal population, i.e. a population of individuals having no diagnosis of RA, is selected and useful statistical characteristics from the reference population are determined and can be used For example, a normal Mean, Range and Standard Deviation for CCL8 protein level is established in a reference population. The normal Mean, Range and Standard Deviation will depend in part on the reference population used, and also in part on the specific assay technique employed and the standardization used in producing the assay. The mean, range and standard deviation can be used to establish a predetermined CCL8 protein level as a threshold value or "cut-off" level, above which is indicative of the presence of RA in a subject, and below which is indicative of the absence of RA in the subject. For example, the cut-off can be the Mean plus two (2) Standard Deviations (obtained from the normal population). It will be understood that different assays may lead to different cut-off values.

In any of the methods described herein, the level of CCL8 protein in the test sample can be measured with further resort to various techniques including mass spectrometry, high performance liquid chromatography, and two-dimensional electrophoresis.

Any of the methods described herein can be advantageously combined with measurements of one or more additional known or heretofore undescribed markers of RA, such as but not limited to C-reactive protein (CRP), a-CCP, CARF IgG, matrix metalloprotease 1 (MMP-1), matrix metalloprotease 3 (MMP-3), serum amyloid A (SAA), Rheumatoid factor (RF), S100, osteopontin, hyaluronic acid (HA), sCD14, angiogenesis markers and products of bone, cartilage or synovium metabolism. Thus CCL8 protein and one or more additional markers, or specific binding partners thereto, can be combined in a marker panel for RA. It will be understood that each additional positive test for an RA marker can provide an increasingly higher level of confidence in a positive test result. Thus, for example, an elevated level of RF in a subject, i.e. an RF level above a predetermined cut-off for RF, in combination with a CCL8 protein level in the subject above a predetermined cut-off for CCL8, will provide a higher level of confidence in a positive diagnosis of RA for that subject than would either of the marker levels alone. Thus the methods also improve the diagnostic accuracy for RA against healthy controls and/or patients suffering from other conditions such as osteoarthritis by measuring in a sample the level of CCL8 protein and at least one additional marker of RA, such that more patients are correctly identified as suffering from RA as compared to an identification based on CCL8 protein or any other single RA marker alone. An RA marker panel comprising at least CCL8 protein and at least one additional RA marker can also be used to evaluate the severity of RA in a subject.

As noted herein above, CCL8 protein and the one or more additional RA markers can be part of an RA marker panel, i.e. two or more markers used in combination to improve the assessment of RA. While any number of markers can be used in an RA marker panel, a useful marker panel will include for example 20 or fewer markers, 15 or fewer markers, 10 or fewer markers, or 8 or fewer markers. Exemplary panels include 3, 4, 5, or 6 markers in total.

A convenient method for determining the sensitivity and specificity of any one marker is the Receiver Operating Characteristic (ROC) analysis. An example of ROC analysis is provided in Example 2 below. The Area Under the Curve (AUC) generated from an ROC plot is a useful measure. AUC values range from 1.0, which indicates a classifier that perfectly distinguishes two different groups, to 0.5, which indicates a classifier that fails to provide any distinction between the two groups. An AUC value approximating 1.0 thus indicates a highly strong classifier. Diagnostic accuracy of any one purported RA marker can be determined by plotting an ROC curve for patients with RA against patients known to be free of RA. A marker with an AUC value of greater than 0.65 as derived from such a plot, is an RA marker.

The present disclosure also encompasses a method for determining the severity of rheumatoid arthritis in a subject comprising determining the presence or absence of an elevated level of CCL8 protein in a test sample obtained from the subject wherein the presence of an elevated level of CCL8 protein indicates that the rheumatoid arthritis in the subject is severe. An elevated level can be for example any level above a predetermined threshold or cut-off value established as described herein above but for severe disease, for example based upon a reference population characterized by the presence of severe RA disease as determined by clinical indicators or other markers of RA. For example, a disease score or index for each subject can be determined that correlates with severity of RA disease and then a population of individuals with a severity score or index above a predetermined cut-off used to establish a CCL8 cut-off for distinguishing severe RA disease.

The present disclosure also encompasses a method for identifying a candidate substance as a therapeutic agent for treating RA. For example, a test substance can be administered to an animal subject having an animal model of RA. Animal models of rheumatoid arthritis (RA) with a proven record of predictability with reference to humans include: adjuvant-induced arthritis (AIA) in rats and collagen-induced arthritis (CIA) in rats and mice (e.g. rat adjuvant arthritis, rat type II collagen arthritis, mouse type II collagen arthritis) and antigen-induced arthritis in several species. Therapeutic agents known to be active in these models include, for example, corticosteroids, methotrexate, non-steroidal anti-inflammatory drugs, cyclosporin A, leflunomide interleukin-1 receptor antagonist (IL-1ra) and soluble TNF receptors. Following administration of the therapeutic agent to the animal subject sample, e.g. a blood, serum or plasma sample is obtained from the animal and the level of CCL8 protein in the test sample measured. The test substance is identified or selected as a candidate substance as a therapeutic agent for treating RA if the level of CCL8 protein in the test sample is lower than the level of CCL8 protein in a test sample from a comparable animal subject not administered the test substance.

In another aspect the present disclosure provides a method for monitoring the effect of any treatment of RA in a subject. Treatments for RA can include drugs, physical therapy and surgery. The methods can be used to evaluate the efficacy of any such treatments but are contemplated primarily for determining the efficacy of drugs, i.e. pharmaceutical compositions, both known and heretofore undescribed for the treatment of RA. Such pharmaceutical compositions include but are not limited to non-steroidal anti-inflammatory drugs (NSAIDs) including over-the-counter NSAIDs such as ibuprofen and naproxen and stronger NSAIDs available by prescription such as the COX-2 inhibitors including Celebrex, Vioxx; steroids including corticosteroids such as prednisone and methylprednisolone; disease-modifying antirheumatic drugs (DMARDs), including but not limited to methotrexate, leflunomide, hydroxychloroquine, sulfasalazine and minocycline; immunosuppressants including but not limited to azathioprine, cyclosporine and cyclophosphamide; TNF-alpha inhibitors including but not limited to etanercept, infliximab, and adalimumab; and other pharmaceutical compositions including but not limited anakinra (Kineret), abatacept (Orencia) and rituximab (Rituxan). Before administration of any pharmaceutical composition and/or other treatment, a first level of CCL8 protein is determined from a first test sample obtained from the subject before the treatment. A second level of CCL8 protein is measured in a second test sample obtained from the subject after the treatment begins, for example after a period of days, weeks or months, and the first CCL8 protein level and second CCL8 level compared. If the second level of CCL8 protein level is lower than the first level of CCL8 protein, it indicates that the treatment has had a therapeutic effect in the subject.

Any anti-CCL8 antibody and any antibody against any other RA marker, as used to detect CCL8 protein and any other RA marker in immunoassays according to the methods disclosed herein, can be a polyclonal antibody, a monoclonal antibody, a chimeric antibody, a human antibody, an affinity maturated antibody or an antibody fragment.

While monoclonal antibodies are highly specific to the analyte/antigen, a polyclonal antibody can preferably be used as the capture (first) antibody to immobilize as much of the analyte/antigen as possible. A monoclonal antibody with inherently higher binding specificity for the analyte/antigen may then preferably be used as the detection (second) antibody. In any case, the capture and detection antibodies preferably recognize two non-overlapping epitopes on the analyte to avoid blockage of, or interference by the capture antibody with the epitope recognized by the detection antibody. Preferably the capture and detection antibodies are capable of binding simultaneously to different epitopes on the analyte, each without interfering with the binding of the other.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, Current Protocols in Immunology, Wiley Interscience).

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naive" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Antibodies for CCL8 and any other RA marker can also be bound to a solid phase, which can be any suitable material with sufficient surface affinity to bind an antibody. The capture antibody can be attached to the solid phase by adsorption, where it is retained by hydrophobic forces. Alternatively, the surface of the solid phase can be activated by chemical processes that cause covalent linkage of the capture antibody to the support. The solid phase can take any of a number of forms, such as a magnetic particle, microparticle, bead, test tube, microtiter plate, cuvette, membrane, a scaffolding molecule, quartz crystal, film, filter paper, disc or a chip.

Any immunoassay used according to the methods of the present disclosure may employ an antibody bound to a detectable label. Detectable labels can include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., Dynabeads™), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3$H, $^{125}$I, $^{35}$S, $^{14}$C, or $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

C. Diagnostic Reagents, Kits and Pharmaceutical Compositions

The present disclosure also contemplates a kit for performing the methods disclosed herein, such as a kit including a diagnostic reagent which includes an anti-CCL8 antibody for measuring a level of CCL8 protein in a test sample. The kit may include additional one or more diagnostic reagents for measuring additional RA markers, such as antibodies against any other RA marker. A kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), a label, and/or any other material useful in sample processing, washing, or conducting any other step of the assay. Tests kits can include an anti-CCL8 antibody bound to a solid phase such as a microtiter plate, and at least one additional marker of RA also bound to the solid phase, for use as an RA marker panel for improving diagnostic accuracy for RA. Test kits according to the present disclosure preferably include instructions for carrying out one or more immunoassays for detecting CCL8 protein and at least one other RA marker. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

An anti-CCL8 antibody or fragment(s) thereof can also be used as an active ingredient in a pharmaceutical composition for the treatment of RA in a subject, or in the manufacture of such a composition, to reduce or eliminate CCL8 protein activity in the subject. A pharmaceutical composition may contain a therapeutically effective amount of an anti-CCL8 antibody along with a pharmaceutically acceptable carrier or excipient. An anti-CCL8 antibody can be combined for example with a therapeutically effective amount of another active ingredient used for the treatment of RA, such as but not limited to non-steroidal anti-inflammatory drugs (NSAIDs) including over-the-counter NSAIDs such as ibuprofen and naproxen and stronger NSAIDs available by prescription such as the COX-2 inhibitors including Celebrex, Vioxx; steroids including corticosteroids such as prednisone and methylprednisolone; disease-modifying antirheumatic drugs (DMARDs), including but not limited to methotrexate, leflunomide, hydroxychloroquine, sulfasalazine and minocycline; immunosuppressants including but not limited to azathioprine, cyclosporine and cyclophosphamide; TNF-alpha inhibitors including but not limited to etanercept, infliximab, and adalimumab; and other pharmaceutical compositions including but not limited anakinra (Kineret), abatacept (Orencia) and rituximab (Rituxan). As used herein, "pharmaceutically acceptable carrier" or "pharmaceutically acceptable excipient" includes any and all solvents, dispersion media, coating, antibacterial and antifungal agents, isotonic and absorption delaying agents, and the like that are physiologically compatible. Examples of pharmaceutically acceptable carriers or excipients include one or more of water, saline, phosphate buffered saline, dextrose, glycerol, ethanol and the like as well as combinations thereof. In many cases, it will be useful to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the of the antibody or antibody portion also may be included. Optionally, disintegrating agents can be included, such as cross-linked polyvinyl pyrrolidone, agar, alginic acid or a salt thereof, such as sodium alginate and the like. In addition to the excipients, the pharmaceutical composition can include one or more of the following, carrier proteins such as serum albumin, buffers, binding agents, sweeteners and other flavoring agents; coloring agents and polyethylene glycol.

The pharmaceutical compositions may take any of a variety of forms, including for example, liquid, semi-solid and solid dosage forms, such as liquid solutions (e.g. injectable and infusible solutions), dispersions or suspensions, tablets, pills, powders, liposomes and suppositories. The preferred dosage form depends on the intended mode of administration and therapeutic application. Compositions can be for example in the form of injectable or infusible solutions, such as compositions similar to those used for passive immunization of humans with other antibodies. Administration can be parenteral (e.g., intravenous, subcutaneous, intraperitoneal, intramuscular). An anti-CCL8 antibody or antibodies in a solution form can be administered by intravenous infusion or injection, or intramuscular or subcutaneous injection. Other suitable routes of administration for the pharmaceutical composition include, but are not limited to, rectal, transdermal, vaginal, transmucosal or intestinal administration.

Therapeutic compositions typically must be sterile and stable under the conditions of manufacture and storage. The composition can be formulated as a solution, microemulsion, dispersion, liposome, or other ordered structure suitable to high drug concentrations. Sterile injectable solutions can be prepared by incorporating the active compound (i.e. antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Anti-CCL8 antibody and antibody fragments can be administered by a variety of methods known in the art, although for many therapeutic applications, administration by intravenous injection or infusion is preferred. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g., Sustained and Controlled Release Drug Delivery Systems, J. R. Robinson, ed., Marcel Dekker, Inc., New York, 1978).

An anti-CCL8 antibody or antibody fragment for treating RA can be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixirs, suspensions, syrups, wafers, and the like. To administer an anti-CCL8 antibody or antibody fragment by other than parenteral administration, it may be necessary to coat the compound with, or co-administer the compound with, a material to prevent its inactivation.

As described herein above, additional active compounds for treating RA can be incorporated into the pharmaceutical compositions. In certain embodiments, an antibody or antibody fragment of the invention is co-formulated with and/or co-administered with one or more active ingredients such as one or more antibodies against one or more additional RA markers. For example, an anti-CCL8 antibody or antibody fragment may be co-formulated and/or co-administered with one or more additional antibodies against an RA marker such as RF, or any other RA marker as described herein. Furthermore, one or more anti-CCL8 antibodies may be used in combination with two or more of recognized therapeutic agents for treating RA as described herein above. Such combination therapies may advantageously utilize lower dosages of each of the administered therapeutic agents, thus avoiding possible toxicities or complications associated with the various monotherapies.

As used herein, the term "therapeutically effective amount" means an amount of antibody or antibody fragment that produces the effects for which it is administered. The exact dose will be ascertainable by one skilled in the art. As known in the art, adjustments based on age, body weight, sex, diet, time of administration, drug interaction and severity of condition may be necessary and will be ascertainable with routine experimentation by those skilled in the art. A therapeutically effective amount is also one in which the therapeutically beneficial effects outweigh any toxic or detrimental effects of the antibody or antibody fragment. A "prophylactically effective amount" refers to an amount effective, at dosages and for periods of time necessary to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of any antibody or antibody component of the pharmaceutical compositions is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

D. Adaptations of the Methods of the Present Disclosure

By way of example, and not of limitation, examples of the present disclosures shall now be given.

EXAMPLE 1

Correlation of CCL8 Serum Levels with Rheumatoid Arthritis Diagnosis

Fifty-nine (59) human serum specimens were obtained from ProMedDx LLC (Norton, Mass.). Of the 59, 39 were from normal subjects, 10 were from patients that had developed human anti-mouse antibodies (HAMA) in response to therapeutic administration of mouse-derived antibodies, and 10 were from subjects with a positive diagnosis of rheumatoid arthritis (RA). For each specimen, CCL8 protein concentration was determined using a CCL8 immunoassay kit (RUO) from Immuno-Biological Laboratories Co., Ltd. (Japan), according to instructions on the package insert in the kit. Table 1 lists CCL8 levels obtained in each RA subject using serial dilution in (a), and (b) with HBR to block reduce interference heterophilic antibody interference.

TABLE 1

CCL8 Levels in RA subjects

|  | CCL8 level (pg/mL) (a) | CCL8 level with HBR (pg/mL) (b) | b/a ratio |
|---|---|---|---|
| RF-c01 | 95 | 93 | 98% |
| RF-c02 | 174 | 177 | 102% |
| RF-c03 | 147 | 149 | 101% |
| RF-c04 | 219 | 211 | 96% |
| RF-c05 | 125 | 124 | 100% |
| RF-c06 | 111 | 136 | 122% |
| RF-c07 | 123 | 149 | 121% |
| RF-c08 | 81 | 89 | 110% |
| RF-c09 | 145 | 151 | 104% |
| RF-c10 | 113 | 120 | 106% |
|  |  | Mean | 106% |

FIG. 1 is a scatter plot of individual CCL8 protein levels measured in the serum samples, with results from normal individuals plotted at left, results from individuals exhibiting a HAMA response plotted at center, and results from individuals with a positive diagnosis of RA plotted at right. For each group of subjects, the mean is indicated by the horizontal line. As shown in FIG. 1, the mean CCL8 level in RA subjects was substantially higher than in either the normal subjects or HAMA subjects. Using a cut off of 94 pg/mL (Mean CCL8 level from Normals+2SD), 90% (9/10) of RA patients showed elevated levels of CCL8 above the cut-off (as determined using serial dilution). Thus, CCL8 showed a high positive rate in detecting RA despite a relatively small number of specimens tested.

EXAMPLE 2

Figure 2:
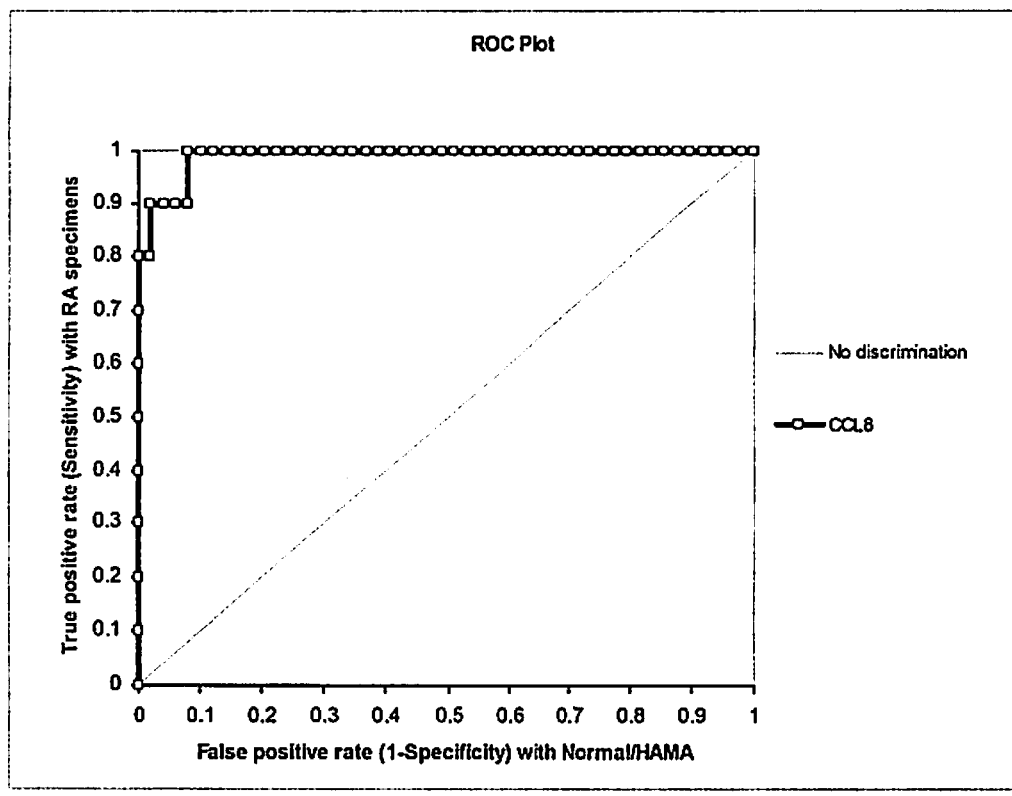
FIG. 2 is a Receiver Operating Characteristic (ROC) plot of observed true positive rate of elevated CCL8 level in RA subjects versus observed false positive rate of elevated CCL8 level in Normal and HAMA subjects.

Low False Positive Rate and Low False Negative Rate of CCL8 Serum Levels in Detecting Rheumatoid Arthritis FIG. 2 is a Receiver Operating Characteristic (ROC) plot of the observed true positive rate of elevated CCL8 level in RA subjects against the observed false positive rate of elevated CCL8 level in Normal and HAMA subjects. The diagonal line across the plot indicates the plot expected from a worst possible prediction method in which CCL8 levels would not discriminate at all between RA subjects and normal or HAMA subjects. A best possible prediction method is expected to yield a point in the upper left corner or coordinate (0,1) of the ROC space, representing 100% sensitivity (no false negatives) and 100% specificity (no false positives). Thus, an area under the curve (AUC) derived from a plot of actual data which approaches the value of 1.0 represents a best possible prediction method. As can be seen in FIG. 2, the AUC is 0.990, indicating that elevated CCL8 level (i.e. a value of CCL8 protein above the cut-off of 94 pg/mL) is a very strong predictive classifier for RA.

The present disclosure illustratively described herein suitably may be practiced in the absence of any element or elements, limitation or limitations which are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method for diagnosing and treating rheumatoid arthritis in a subject comprising:
   a. measuring a level of chemokine c-c motif ligand 8 (CCL8) protein in a serum sample obtained from the subject, wherein the level of CCL8 protein in the serum sample is measured by solid phase sandwich ELISA with an anti-CCL8 antibody and a plate reader;
   b. assessing the subject for presence or absence of at least four of the following clinical indicators of rheumatoid arthritis: (1) morning stiffness for at least one hour, (2) arthritis of three or more joint areas, (3) arthritis of hand joints, (4) symmetrical arthritis, (5) rheumatoid nodules, (6) serum rheumatoid factor ("RF"), or (7) radiographic changes;
   c. detecting a level of CCL8 protein in the serum sample of the subject that is greater than 94 pg/mL and the presence of at least four clinical indicators of rheumatoid arthritis selected from step b. in the subject to thereby determine the presence of rheumatoid arthritis in the subject; and
   d. administering a composition comprising an anti-CCL8 antibody or an antigen-binding fragment of the anti-CCL8 antibody at a concentration effective to treat the subject when the subject is determined to have rheumatoid arthritis according to step (c).

2. The method according to claim 1, further comprising measuring a level of one or more markers of rheumatoid arthritis in the serum sample, wherein the markers are selected from the group consisting of: C-reactive protein (CRP), anti-cyclic citrullinated peptide (a-CCP), anti-agalactosyl IgG antibody (CARF IgG), matrix metalloprotease 3 (MMP-3), and rheumatoid factor, and wherein the measured level of CCL8 protein in step c and an increased level of the one or more rheumatoid arthritis markers in the serum sample of the subject further indicates presence of rheumatoid arthritis in the subject.

3. A method for monitoring treatment of rheumatoid arthritis in a subject comprising:
   a. measuring a first level of chemokine c-c motif ligand 8 (CCL8) protein in a first serum sample obtained from the subject before treatment and detecting a level of CCL8 protein that is greater than 94 pg/mL to determine presence of rheumatoid arthritis in the subject;

b. measuring a second level of CCL8 protein in a second serum sample obtained from the subject after the treatment begins;

c. comparing the measured first level of CCL8 protein in step a. and the measured second level of CCL8 protein in step b., wherein a second level of CCL8 protein that is lower than the first level of CCL8 protein is indicative of a therapeutic treatment of rheumatoid arthritis in the subject; and d. altering the treatment in the subject if the measured second level of CCL8 protein is greater than 94 pg/mL, wherein altering the treatment includes administering a composition comprising an anti-CCL8 antibody or an antigen-binding fragment of the anti-CCL8 antibody at a concentration effective to treat the subject having rheumatoid arthritis, wherein the levels of CCL8 protein in the first and second serum samples are measured by solid phase sandwich ELISA with an anti-CCL8 antibody and a plate reader.

* * * * *